United States Patent [19]

Konrad et al.

[11] Patent Number: 4,588,410
[45] Date of Patent: May 13, 1986

[54] NOVEL 2-HYDROXY-4-AMINOBENZENES, METHOD FOR THEIR MANUFACTURING AND HAIR COLORING AGENTS CONTAINING THESE COMPOUNDS

[75] Inventors: Eugen Konrad, Darmstadt, Fed. Rep. of Germany; Hans-Jürgen Braun, Marly; Herbert Mager, Fribourg, both of Switzerland

[73] Assignee: Wella Aktiengesellschaft, Darmstadt, Fed. Rep. of Germany

[21] Appl. No.: 517,524

[22] PCT Filed: Nov. 15, 1982

[86] PCT No.: PCT/EP82/00245
§ 371 Date: Jul. 18, 1983
§ 102(e) Date: Jul. 18, 1983

[87] PCT Pub. No.: WO83/01771
PCT Pub. Date: May 26, 1983

[30] Foreign Application Priority Data

Nov. 19, 1981 [DE] Fed. Rep. of Germany ....... 3145811

[51] Int. Cl.$^4$ ................. A61K 7/13; C07L 91/40
[52] U.S. Cl. ....................................... 8/421; 8/405; 8/406; 564/413; 564/418; 564/443; 564/441
[58] Field of Search .......... 564/443, 413, 418, 441; 8/405, 406, 421; 260/206, 501.1

[56] References Cited

U.S. PATENT DOCUMENTS 3,052,722 9/1972 Ashley et al. ............ 564/443
3,834,866 9/1974 Pum ........................ 8/421

FOREIGN PATENT DOCUMENTS 6810595 1/1969 Netherlands .

Primary Examiner—Charles F. Warren
Assistant Examiner—John A. Sopp
Attorney, Agent, or Firm—Michael J. Striker

[57] ABSTRACT 2-hydroxy-4-aminobenzene are disclosed, useful as oxidative hair coloring substances. These are of the formula

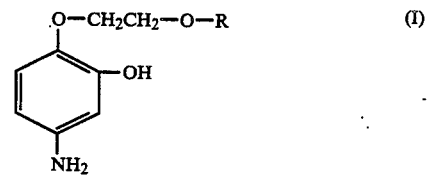

wherein R is hydrogen, methyl or hydroxyethel.

19 Claims, No Drawings

NOVEL 2-HYDROXY-4-AMINOBENZENES, METHOD FOR THEIR MANUFACTURING AND HAIR COLORING AGENTS CONTAINING THESE COMPOUNDS

BACKGROUND OF THE INVENTION

The subject invention relates to novel 2-hydroxy-4-aminobenzenes of the general formula

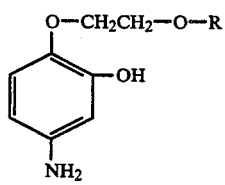

wherein R is a hydrogen atom, a methyl group or a hydroxyethyl group.

The subject invention relates also to the salts formed by the compounds of the general formula with anorganic or organic acids like, the hydrochlorides, hydrobromides or sulfates or the corresponding phenolates.

SUMMARY OF THE INVENTION

The novel compounds in accordance with the invention are produced based on a 4-nitro-1,2-methylene dioxybenzene, in that it is heated in a solution of sodium in dry ethyl glycol (a), or diethyl glycol (b), or 2-methoxyethanol (c) for a few hours, in particular for 3 hours, to a temperature of 120° C., the generated solution is then absorbed in water after cooling, then it is filtered, the filtrate is acidified and the precipitated purified 2-hydroxy-4-nitrobenzene derivative of the formula

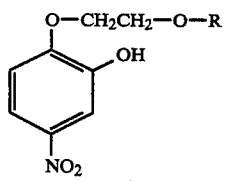

wherein R is a hydrogen atom, a methyl group or a hydroxyethyl group which is hydrated in the presence of a catalyst, preferably palladium in a known manner to 1-(2'-hydroxyethoxy)-2-hydroxy-4-aminobenzenes (a), or 1-(hydroxy-bis-ethoxy)-2-hydroxy-4-aminobenzenes (b), or 1-(2'-methoxy-ethoxy)-2-hydroxy-4-aminobenzenes (c).

The novel compounds in accordance with the invention represent oxidative color preliminary steps which are very well suited for coloring hair.

The so-called oxydation colors for coloring hair which are created by an oxidative coupling of a developer component with a coupler component play a preferred role because of their intensive colors and their very good fast characteristics. Customarily, 2,5-diaminotoluene, 4-aminophenol and the 1,4-diaminotoluene are used as the developer substances; however 2,5-diaminotoluene, 3-methyl-4-aminophenol, 2,5-diaminobenzylalcohol and 2(β-hydroxyethyl)-1,4-diaminotoluene have attained a certain importance. Also, the tetraaminopyrimidin may be used as a developer.

Resorcin, 4-chlorresorcin, m-aminophenol, 5-amino-2-methylhenol, 1-naphthol as well as derivatives of the m-phenyldiamine, for example, 2-amino-4-(β-hydroxyethylamino)anisole or 2,4-diaminophenoxyethanol are known as preferably used coupler substances.

A number of particular requirements are made with respect to oxydation colors which are used for coloring human hair. From the toxicological and the dermatological point of view they must be unobjectionable and enable the attainment of colorings in the desired intensity. Furthermore, it is a requirement that a wide spectrum of different color shades can be generated by combining suitable developers and coupler components. Furthermore, a good light, permanent, acid and friction fastness is required for the attainable hair colorings. In any case, such hair colorings must remain stable for at least 4-6 weeks without influence of light, chemical agents and friction.

Colors which can be directly absorbed by the hair are also of importance, besides the mentioned preliminary colors. With these directly absorbed colors, in particular aromatic nitrocolors, yellow, orange, red and violet colors are attained.

Preferably, resorcin and m-aminophenol as a coupler in conjunction with p-phenyldiamines or 2,5-diaminotoluene are used as a developer for generating natural color tones. The yellow coloring caused by resorcin is covered by adding m-aminophenol and in this manner the color tone is adjusted as a whole to a warmer color tone.

However, if one would like to create fashionable tones, the use of m-aminophenol is less suitable since it generates only a very weak color tone together with the p-aminopenol and does not result in a red tone but rather a violet tone with the customary p-diamines like, for example, the 2,5-diaminotoluene or the 2,5-diaminobenzene alcohol.

It is therefore an object of the invention to make available novel color effective compounds as coupler substances which substantially eliminate the disadvantages of the m-aminophenol and result in cooling agents which meet the requirements in an optimum manner.

The invention also relates to hair coloring agents containing the novel compounds as well as a method for coloring of hair.

In addition, the compounds in accordance with the invention should be protective for the skin of the hands and the head.

The object of the invention is solved by 2-hydroxy-4-aminobenzenes of the general formula

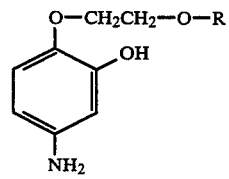

wherein R is a hydrogen atom, a methyl group or a hydroxyethyl group, as well as their acid addition salts with anorganic o organic acids or the phenolates thereof.

It has been shown that the disadvantages described with respect to the m-aminophenol can be eliminated in a simple manner by using the inventive compounds, in particular by using i-(2'hydroxyethoxy)-2-hydroxy-4- aminobenzene as a coupler substance. For example, the 1-(2'-hydroxyethoxy)-2-hydroxy-4-aminobenzene together with the p-aminophenol as developer substance results in a very intensive fashionable copper tone which can be shaded depending on the requirements.

In addition, it had been shown that the novel compounds in accordance with the invention generate noticeably less violet shaded tones in comparison with the m-aminophenol with the customary p-diamines like, for example, the known 2,5-diaminotoluene, so that therefore the inventive coupler substances with p-diamines result in improved possibilities of use for red shades.

In view of the described new possibilities for generating red tones it is also possible to replace the red coloring nitro-colors while simultaneously attaining more uniform and improved colorings. The replacement of the nitro colors is of great importance since these colors create nonuniform colorings on differently damaged hair and very often insufficiently colors the porous hair tips.

In addition to the stated preferred fields of use of the novel coupler substances, they also can be used in combination with the developer substances 2,5-diaminobenzene and tetraamino pyrimidine, whereby interesting violet tones are created.

The novel coupler substances in accordance with the invention may be used as such or in form of their salts with anorganic or organic acids like, for example, the chlorides, sulfates, phosphates, acetates, propionates, lactates, citrates or in form of their salts with base, for example, as alkaliphenolates.

The coupler substances in accordance with the invention are generally used in about a molar amount in relation to the used developer substances. Even if the molar use is shown to be advantageous, it is not disadvantageous when the coupler substances are used at a certain excess or fall below the molar amount. Furthermore, it is not required that the developer compounds and the coupler compounds represent uniform products, rather the developer compounds can represent a mixture of known developer substances and the coupler components may also represent a mixture of the inventive compounds with known coupler substances.

The novel inventive coupler substances of which the 1-(2'-hydroxyethoxy)-2-hydroxy-4-aminobenzene is preferred should be present in the hair coloring agents in a concentration of about 0.1 to 5.0 by weight %, in particular 0,3 to 3.0 by weight %.

The claimed hair coloring agent may contain self coupling preliminary colors like, for example, 2-amino-5-methylphenol, 2-amino-6-methylphenol, 2-amino-5-ethoxyphenol or also 2-(-hydroxyethylamino)-5-aminopyridin and 2-propylamino-5-aminopyridin.

In addition further customary cosmetic additives may be contained in the hair coloring agent, for example, antioxidants like, ascorbin acid or sodium sulfate, perfume oils, complex formers, wetting agents, emulsifiers, thickeners, caring agent and others.

The type of preparation may be a solution, in particular a watery or watery-alcoholic solution. However, the particularly preferred types of preparation should be a creme, a gel or an emulsion.

Its composition represents a mixture of the color components together with the additives customary for such preparations.

Customary additives in solutions, cremes, emulsions or gels are, for example, solvents like, water, lower aliphatic alcohols, for example, ethanol, propanol and isopropanol, or glykols like, glycerin and glykolether like, propyl glykol, furthermore, wetting agents or emulsifiers from the classes of the anionic, kationic, amphoteric or noniorgenic surface active substances like, fatty alcohol sulfates, alkyl sulfonates, alkyl benzol sulfonates, alkyl trimethyl ammonium salts, alkylbetaine, oxethylized nonyphenols, fatty acid alkanolamides, oxethylized fatty acid esters, furthermore, thickeners like, higher fatty alcohols, starch, cellulose derivatives, vaseline, paraffin oil and fatty acids as well as caring agents like, lanolin derivatives, cholesterin, pantothen acid and betain. The mentioned constituents are used in amounts customary for such purposes, for example, the wetting agents and emulsifiers in concentrations of about 0,5 to 30 by weight %, while the thickener may be contained in an amount of about 0,1 to 20 by weight % in the preparations.

Depending on the composition the hair coloring agents in accordance with the invention may be slightly acid, neutral or alkalic reacting. In particular, they have a pH-value in the alkaline range between 8,0 and 11,5, whereby the adjustment is performed preferably with ammonia. However, organic amines may be used, for example, monoethanolamin and triethanolamin or organic base like, sodium hhydroxide and potassium hydroxide.

In the invention method for the oxidative coloring of hair one admixes the hair coloring agents which contain a combination of developer substances known in the hair coloring with at least a 2-hydroxy-4-aminobenzol of the formula (i) as coupler substances, as well as additional known coupler substances with an oxidation agent shortly before use and applies this mixture on the hair. As an oxydation agent for developing the hair coloring one mainly uses hydrogen peroxide, for example, as a 6% aqueous solution or its addition compounds of urea, melamin or sodium borate. The mixture should act on the hair at about 15° to 50° for about 10 to 45 minutes, preferably 30 minutes, thereafter the hair is rinsed with water and is dried. If necessary, the hair is washed with a shampoo subsequent to the rinsing and is afterrinsed with a light organic acid, for example, citric acid or tartaric acid.

During use the novel coupler substances they produce in accordance with claim 1 very intensive fashionable color tones ranging from copper to red, in conjunction with the developer substances generally used for the oxidation hair coloring, and therefore represent a substantial enrichment of the oxidative hair coloring possibilities. In addition, the 2-hydroxy-4-aminobenzoles of the general formula (I) are characterized by very good fast characteristics of the coloring attained therewith, a good solubility in water and a good storage stability.

The inventive coupler substances of formula (I) are particularly suitable for generating fashionable tones like, a hazelnut brown, a Tizian red, as well as mahagony or violet tones.

The subsequent examples will explain the subject matter of the invention in more detail.

EXAMPLES FOR THE MANUFACTURING OF THE NOVEL COMPOUNDS

EXAMPLE 1

Manufacturing of 1-(2'-hydroxyetoxy)-2-hydroxy-4-aminobenzene of the formula

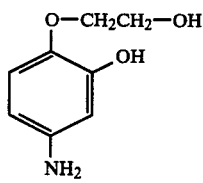

1,7 g (74 mMol) sodium are dissolved in 80 ml dry ethylene glykol and 6,8 g (40 mMol) 4-nitro-1,2-methyldioxybenzene are added to the solution. After the mixture was heated to 120° C. for 3 hours, the dark red cooled off solution is mixed with 400 ml water, it is filtrated and the filtrate is acidified with 2n-hydrochloric acid. Thereby, the 1-(2'-hydroxyethoxy)-2-hydroxy-4-nitrobenzene is precipitated. The prodact is drawn off, washed with water and dried. The raw product is crystallized from an ethanol-water mixture and is dried for 24 hours in a vacuum. The yield of the product which melts at 159° to 161° C. was 5,84 g (29 mMol)=72% in relation to the charged 4-nitro-1,2-methyldioxybenzol.

For manufacturing the 1-(2-hydroxyethoxy)-2-hydroxy-4-aminobenzene, 1,8 g (9 mMol) of the nitrobenzene derivative are dissolved in 220 ml etanol and hydrated with 0,12 g palladium onto active carbon (10% palladium). After finishing the hydrogen absorption the filtering off from the catalyst is started and the filtrate is concentrated. The remaining oil is distilled in a bulbed tube at 225° C./0,07 mbar.

Yield: 1,2 g (7 mMol; 77%).

| CHN-analysis: | C % | H % | N % |
|---|---|---|---|
| $C_8H_{11}NO_3$ calc: | 56,80 | 6,55 | 8,28 |
| found: | 56,72 | 6,59 | 8,18 |

For an improved handling of the substance it is advantageous to convert it into its hydrochloride or its sulfate.

(a) Hydrochloride 1,2 g (7 mMol) of the free base are dissolved in 50 ml isopropanol and mixed with 5 drops of a 37% aqueous hydrochloric acid solution. The hydrochloride precipitates as a white fine crystalline powder when adding diathyl ether.

Yield: 1,18 g (5,7 mMol; 63% in relation to the nitro preliminary color).

The hydrochloride decomposes at 190° C.

| CHNCl-analysis: | C % | H % | N % | Cl % |
|---|---|---|---|---|
| $C_8H_{12}ClNO_3$ calc: | 46,73 | 5,88 | 6,81 | 17,24 |
| found: | 46,62 | 5,91 | 6,73 | 17,40 |

(b) Sulfate 2,3 g (13 mMol) of the free base are dissolved in 80 ml isopropanol. The sulfate is precipitated after an addition of some millimeters 2n-hydrochloric acid. It is drawn off, washed with isopropanol and dried. The yield is 2,0 g (9 mMol)=70%, relating to the charged free base).

Titration: Weighed portion: 41,2 mg, Discharge: 0,01 n NaOH, $(C_8H_{11}NO_3 x \frac{1}{2} H_2SO_4)$ calc: 18,90 ml, found: 18,25 ml.

EXAMPLE 2

Manufacturing of 1-(hydroxy-bis-ethoxy)-2-hydroxy-4-aminobenzene of the formula

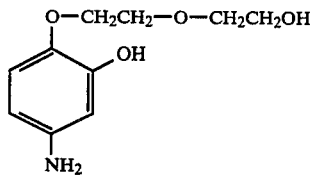

The method is analog to example 1, with the difference that instead of ethylene glykol, 80 ml diethylene glykol is used.

(a) 1-(hydroxy-bis-ethoxy)-2-hydroxy-4-nitrobenzene melting point: 115°-116° C.

| CHN-analysis: | % C | % H | % N |
|---|---|---|---|
| $(C_{10}H_{13}NO_6)$ ber: | 49,38 | 5,39 | 5,76 |
| gef: | 49,28 | 5,35 | 5,72 |

(b) 1-(hydroxy-bis-ethoxy)-2-hydroxy-4-aminobenzene, boiling point in the bulb tube: 220°-230° C./0,08 mbar. The oil solidifies like glass.

| CHN-analysis of the sulfate: | % C | % H | % N |
|---|---|---|---|
| $(C_{10}H_{15}NO_4 x \frac{1}{2} H_2SO_4)$ calc: | 45,80 | 6,15 | 5,34 |
| found: | 44,36 | 6,17 | 5,32 |

EXAMPLE 3

Manufacturing of 1-(2'-methoxyethoxy)-2-hydroxy-4-aminobenzene of the formula

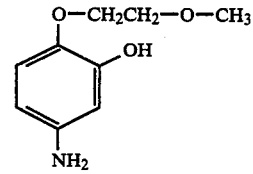

The manufacturing is performed analog to the mode of operation in example 1, with the difference that instead of ethylene glykol 80 ml 2-methoxyethanol are used.

(a) 1-(methoxyethoxy)-2-hydroxy-4-nitrobenzene melting point: 90°-91° C.

| CHN-analysis: | % C | % H | % N |
|---|---|---|---|
| $(C_9H_{11}NO_5)$ calc: | 50,71 | 5,20 | 6,57 |
| found: | 50,80 | 5,23 | 6,73 |

(b) Hydrochloride

The hydrochloride of the attained 1-(2'-methoxyethoxy)-2-hydroxy-4-aminobenzene melts at a decomposition at a temperature of 153° C.

| CHN-analysis: | % C | % H | % N |
|---|---|---|---|
| $(C_9H_{14}ClNO_3)$ calc: | 46,21 | 6,42 | 6,38 |
| found: | 46,30 | 6,36 | 6,48 |

APPLICATION EXAMPLES

EXAMPLE A

Hair Coloring Agent in Cream Form

| | |
|---|---|
| 0,40 g | 1-(2'-hydroxyethoxy)-2-hydroxy-4-aminobenzene hydrochloride |
| 0,30 g | 1,4-diaminobenzene |
| 0,30 g | 2-amino-4,6-dinitrophenol (picramic acid) |
| 0,30 g | sodium sulfate, free of water |
| 3,50 g | laurylalcohol-diglykol ether sulfate, sodium salt (28% aqueous solution) |
| 15,0 g | cetylalcohol |
| 4,0 g | ammonia, 25% |
| 76,2 g | water |
| 100.00 g | |

50 g of the aforementioned hair coloring agent are admixed shortly before use with 50 g hydrogen peroxide solution, 6%. The mixture is left on blond natural hair for 30 minutes at 40° C. Thereafter, the coloring mass is rinsed out, the hair is shampooed and dried. It attained an intensive mahagony coloration.

EXAMPLE B

Hair Coloring Solution

| | |
|---|---|
| 1.00 g | 1-(2'-hydroxyethoxy)-hydroxy-4-aminobenzol-hydrochloride |
| 0,50 g | p-aminophenol |
| 10,0 g | laurylalcohol-diglykol ether sulfate, sodium salt (28% watery solution) |
| 10,0 g | isopropanol |
| 0,3 g | sodium sulfite, free of water |
| 10,0 g | ammonia, 25% |
| 68,2 g | water |
| 100,0 g | |

50 g of the aforementioned hair coloring agent are admixed with 50 g hydrogen peroxide solution, 6% before use and applied on blond natural hair. After an application time of 30 minutes at 40° C. the hair had received a color rich tizian red coloration, after rinsing, shampooing and drying.

EXAMPLE C

Hair Coloring Gel

| | |
|---|---|
| 0,70 g | 1-(2'-hydroxyethoxy)-2-hydroxy-4-aminobenzene hydrochloride |
| 0,50 g | tetraaminopyrimidin |
| 15,0 g | oleic acid |
| 7,0 g | isopropanol |
| 0,3 g | ascorbic acid |
| 9,0 g | ammonia, 25% |
| 67,5 g | water |
| 100,0 g | |

50 g of the hair coloring agent are mixed with 50 g hydrogen peroxide solution, 6% shortly before being applied on blond natural hair for about 30 minutes at 40° C. After rinsing, shampooing and drying the hair is colored intensively purple.

All percentage numbers stated in the subject application are percentages by weight.

It will be understood that each of the elements described above, or two or more together, may also find a useful application in other types of constructions differing from the types described above.

While the invention has been illustrated and described as embodied in a screen printing machine, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. 2-hydroxy-4-aminobenzenes of the general formula

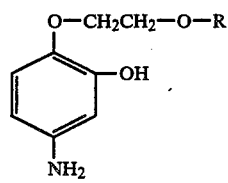

(I)

wherein R is a hydrogen, a methyl group or a hydroxy ethyl group.

2. The acid addition salts of the compounds of 1 with anorganic or organic acids.

3. The phenolates of the compounds of claim 1.

4. 1-(2'-hydroxyethoxy)-2-hydroxy-4-aminobenzene.

5. A hair coloring agent, comprising: a combination of developer substances known in hair coloring with at least one of the compounds in accordance with claim 1 as a coupler substance.

6. An agent as defined in claim 5, wherein the coupler substance is 1-(2'-hydroxyethoxy)-2-hydroxy-4-aminobenzene.

7. An agent as defined in claim 5, wherein the compounds in accordance with claim 1 are present in a concentration of about 0.1 to 5.0 by weight%.

8. An agent as defined in claim 7, wherein the compounds in accordance with claim 1 are present in a concentration of 0.3 to 3.0 by weight%.

9. An agent as defined in claim 5, wherein as developer substances at least one of the compounds selected from the group consisting of 1,4-diaminobenzene, 2,5-diaminotoluene, 2,5-diaminobenzyl alcohol, 2-(-hydroxyethyl)-1,4-diaminobenzene, 4-aminophenol, 3-methyl-4-aminophenol, 2,5-diaminoanisol and tetraaminopyrimidin is used.

10. An agent as defined in claim 5, wherein the coupler substance is at least one compound selected from the group consisting of 1-naphthol, 4-methoxy-1-naphthol, resorcin, 4-chlorresorcin, 4,6-dichlorresorcin, 2-methylresorcin, 4-hydroxy-1,2-methyldioxybenzene, 4-(β-hydroxyethylamino)-1,2-methyldioxybenzene, 4-amino-1,2-methyldioxybenzene, 5-amino-2-methylphenol, 2,4-diaminophenoxyethanol, 2-amino-4-(β-hydroxyethylamino)anisol and 2-(γ-hydroxyprophyl)-5-methylphenol.

11. An agent as defined in claim 5, wherein the total amount of the contained developer substance-coupler substance-combination is about 0.1 to 6.0 by weight%.

12. An agent as defined in claim 11, wherein the total amount of the contained developer substance-coupler substance combination is 0.5 to 3.0 by weight%.

13. An agent as defined in claim 5; and further comprising color constituents selected from the group consisting of 2-amino-5-methylphenol, 2-amino-6-methylphenol, 2-amino-5-ethoxyphenol, 2-($\beta$-hydroxyethylamino)-5-amino-pyridin or 2-propylamino-5-aminopyridin.

14. An agent as defined in claim 5; and further comprising at least one of the direct absorbing colors selected from the group consisting of Diamond Fuchsin (C.I. 42 510), Leather Ruby HF (C.I. 42 520), 2-amino-4,6-dinitrophenol, -nitro-4-($\beta$-hydroxyethylamino)-anilin, 2-amino-4-nitrophenol, Acid Brown 4 (C.I. 14 805), Acid Blue 135 (C.I. 13 385), Disperse Red 15 (C.I. 60 710), Disperse Violet 1 (C.I. 61 100), 1,4,5,8-tetraaminoanthrachinon and 1,4-diamino-anthrachinon.

15. An agent as defined in claim 5; and further comprising antioxydants.

16. An agent as defined in claim 15, wherein the oxydants are ascorbic acid or sodium sulfite.

17. An agent as defined in claim 5; and further comprising wetting agents.

18. An agent as defined in claim 5; and further comprising emulsifiers.

19. An agent as defined in claim 5; and further comprising thickeners.

* * * * *